(12) United States Patent
Cremer et al.

(10) Patent No.: US 10,517,658 B2
(45) Date of Patent: Dec. 31, 2019

(54) BONE PLATE WITH ELONGATED GUIDING CHANNELS

(71) Applicant: Stryker European Holdings I, LLC, Kalamazoo, MI (US)

(72) Inventors: Axel Bernhard Cremer, Pleasantville, NY (US); Jan Heinsohn, Hoboken, NJ (US); Nicole Westin, Chicago, IL (US)

(73) Assignee: Stryker European Holdings I, LLC, Kalamazoo, MI (US)

(*) Notice: Subject to any disclaimer, the term of this patent is extended or adjusted under 35 U.S.C. 154(b) by 463 days.

(21) Appl. No.: 15/389,644

(22) Filed: Dec. 23, 2016

(65) Prior Publication Data

US 2017/0181780 A1 Jun. 29, 2017

(30) Foreign Application Priority Data

Dec. 23, 2015 (EP) .................................... 15003672

(51) Int. Cl.
*A61B 17/80* (2006.01)
*A61B 17/82* (2006.01)

(52) U.S. Cl.
CPC ........ *A61B 17/8028* (2013.01); *A61B 17/809* (2013.01); *A61B 17/8057* (2013.01); *A61B 17/82* (2013.01)

(58) Field of Classification Search
CPC . A61B 17/80; A61B 17/8028; A61B 17/8052; A61B 17/8057; A61B 17/8061; A61B 17/809; A61B 17/82
See application file for complete search history.

(56) References Cited

U.S. PATENT DOCUMENTS

| 5,190,545 | A |   | 3/1993 | Corsi et al. |              |
|-----------|---|---|--------|--------------|--------------|
| 5,324,291 | A | * | 6/1994 | Ries         | A61B 17/8061 |
|           |   |   |        |              | 606/297      |
| 5,665,089 | A | * | 9/1997 | Dall         | A61B 17/80   |
|           |   |   |        |              | 606/309      |
| 5,741,259 | A | * | 4/1998 | Chan         | A61B 17/82   |
|           |   |   |        |              | 606/103      |

(Continued)

FOREIGN PATENT DOCUMENTS

| CH | 701346 A2  | 12/2010 |
|----|------------|---------|
| CN | 103829995 A | 6/2014 |

(Continued)

OTHER PUBLICATIONS

Extended European Search Report for Application No. EP15003672 dated Aug. 31, 2016.

*Primary Examiner* — Eric S Gibson
(74) *Attorney, Agent, or Firm* — Lerner, David, Littenberg, Krumholz & Mentlik, LLP (57) ABSTRACT

A bone plate has bone facing side, a front side being arranged substantially opposite to and facing away from the bone facing side, and at least a first and a second elongated guiding channel. The first and second guiding channels are configured to receive a flexible elongated member such as, for example, a cerclage wire, and the first and second guiding channel are each further configured to guide the elongated member along a respective first and second guiding channel axis (A, B) from a first to a second lateral region of the bone plate. The first and second guiding channel axes (A, B) cross each other in at least one region of the bone plate outer front side.

23 Claims, 4 Drawing Sheets

(56) References Cited

U.S. PATENT DOCUMENTS

| | | | | |
|---|---|---|---|---|
| 6,127,596 A * | 10/2000 | Brown | A61F 2/30739 | 623/16.11 |
| 6,338,734 B1 * | 1/2002 | Burke | A61B 17/74 | 606/280 |
| 8,142,434 B2 | 3/2012 | Bluechel | | |
| 8,343,155 B2 | 1/2013 | Fisher et al. | | |
| 9,119,682 B2 | 9/2015 | Stoll et al. | | |
| 9,549,768 B2 * | 1/2017 | Finley | A61B 17/8004 | |
| 2004/0225291 A1 * | 11/2004 | Schwammberger | A61B 17/80 | 606/71 |
| 2005/0015090 A1 * | 1/2005 | Silverman | A61B 17/80 | 606/71 |
| 2009/0287215 A1 * | 11/2009 | Fisher | A61B 17/80 | 606/71 |
| 2009/0312758 A1 * | 12/2009 | Petit | A61B 17/74 | 606/60 |
| 2010/0004691 A1 | 1/2010 | Amato et al. | | |
| 2010/0100131 A1 | 4/2010 | Wallenstein | | |
| 2010/0234896 A1 * | 9/2010 | Lorenz | A61B 17/74 | 606/286 |
| 2011/0137314 A1 * | 6/2011 | Kuster | A61B 17/74 | 606/70 |
| 2013/0197520 A1 * | 8/2013 | Linares | A61B 17/82 | 606/74 |
| 2013/0289564 A1 * | 10/2013 | Bernstein | A61B 17/82 | 606/74 |
| 2013/0304133 A1 * | 11/2013 | Trauner | A61B 17/82 | 606/301 |
| 2014/0243837 A1 * | 8/2014 | Mebarak | A61B 17/1728 | 606/96 |
| 2014/0243841 A1 * | 8/2014 | Cavallazzi | A61B 17/8869 | 606/103 |
| 2014/0243901 A1 * | 8/2014 | Mebarak | A61B 17/1728 | 606/281 |
| 2014/0243905 A1 * | 8/2014 | Cavallazzi | A61B 17/746 | 606/286 |
| 2014/0243907 A1 * | 8/2014 | Cavallazzi | A61B 17/74 | 606/286 |
| 2016/0143663 A1 * | 5/2016 | Schemitsch | A61B 17/683 | 606/71 |
| 2017/0181780 A1 * | 6/2017 | Cremer | A61B 17/8028 | |
| 2017/0209190 A1 * | 7/2017 | Goodwin, Jr. | A61B 17/8004 | |
| 2017/0215932 A1 * | 8/2017 | Shin | A61B 17/8061 | |
| 2018/0161083 A1 * | 6/2018 | Kobayashi | A61B 17/809 | |
| 2019/0059965 A1 * | 2/2019 | Gausepohl | A61B 17/8085 | |

FOREIGN PATENT DOCUMENTS

| | | |
|---|---|---|
| DE | 20109273 U1 | 8/2001 |
| WO | 2007047467 A1 | 4/2007 |
| WO | 2011006228 A1 | 1/2011 |

* cited by examiner

BONE PLATE WITH ELONGATED GUIDING CHANNELS

CROSS-REFERENCE TO RELATED APPLICATIONS

This application claims the benefit of the filing date of European Patent Application No. 15 003 672.1 filed Dec. 23, 2015, the disclosure of which is hereby incorporated herein by reference.

BACKGROUND OF THE INVENTION

The present disclosure generally relates to bone plates. In particular, a bone plate as well as a bone plate system and a surgical kit assembly comprising the bone plate are described.

To promote the healing process of a damaged or fragmented bone, bone plates are commonly attached to an outside surface of the bone. The bone plates act as stabilizing elements for the damaged area. In addition, they may help to position fragmented bone sections relative to one another.

For attaching a bone plate to a bone, various fixation techniques have been suggested. For example, screws may be applied which are inserted in through-holes of the bone plate and then screwed into an adjacent bone portion. Likewise, circumferential wires can be wound around a cross-section of the bone and a bone plate arranged at the bone. The wires are then tightened to secure the bone plate at the bone and to avoid a relative movement therebetween.

U.S. Pat. No. 5,190,545 discloses an elongated bone plate which is configured to be arranged at an outer surface of a fragmented bone. The bone plate is fixed by winding a circumferential wire around a cross-section of the bone and through positioning inserts of the bone plate which receive and accommodate the circumferential wire. The wire is then tightened by means of a crimp sleeve.

U.S. Pat. No. 5,665,089 discloses a similar bone plate which is held at the bone by means of circumferential wires. In this case, the wires are inserted into through-holes extending between different lateral regions of the bone plate.

Similar solutions are known from U.S. Pat. Nos. 8,343, 155 B2, 5,324,291 and 5,741,259.

BRIEF SUMMARY OF THE INVENTION

There is a need for a bone plate which is easy to use and can be reliably attached to a bone.

According to one aspect, a bone plate is provided, comprising a bone facing side, a front side being arranged substantially opposite to and facing away from the bone facing side, and at least a first and a second elongated guiding channel, the first and second guiding channel each being configured to receive a flexible elongated member, the first and second guiding channel each further being configured to guide said elongated member along a respective first and second guiding channel axis from a first to a second lateral region of the bone plate, and the first and second guiding channel axes crossing each other in at least one region of the bone plate.

The bone plate may be configured with a generally rectangular, oval or circular outline, said outline confining and/or being defined by at least one of the front side or the bone facing side. The bone plate can be anatomically pre-shaped. In one variant, the bone plate has a convexly curved and/or outwardly bulged shape with the front side forming a radially outer portion and the bone facing side forming a radially inner portion of the bone plate.

The bone plate may further comprise at least one through-hole which is configured to receive a screw for fixing the bone plate to an adjacent bone. The through-hole may comprise a thread for engaging with the screw (e.g., with a complementary thread at a screw head). Additionally, or as an alternative, the through-hole may comprise a feature (e.g., a circumferential lip or circumferential protrusions) that permit to lock the screw with the plate at a desired oblique relationship.

The first and second guiding channels can be configured as a free space being provided inside of and/or at the bone plate. For example, the guiding channels may comprise elongated through-holes extending through the bone plate. In one variant, said through-holes extend close to or just below of the front side. The guiding channels can also comprise at least one section that is directly formed in or at the front side. Of course, the guiding channels can also be configured different from one another. Also, they can be configured with varying cross-sectional shapes and/or dimensions along their respective guiding channel axis.

In general, any member or section of the bone plate which provides and/or confines a free space through which the first and second guiding channel axes extend can be considered as forming at least a portion of the guiding channels. For example, the guiding channels may largely be formed in a main body of the bone plate. The main body may, for example, be formed as a one-piece member. Similarly, additional members attached to said main body may define at least a portion of the guiding channels, such as an additional cap member as described below.

The flexible elongated member can be provided in form of a wire or thread. The guiding channels may be configured to receive, accommodate and/or guide said elongated member with a predefined course across the bone plate.

The first and second lateral regions of the bone plate between which the guiding channels extend can be arranged substantially opposite to one another. In one example, the bone plate is configured with a substantially rectangular or oval outline comprising two oppositely arranged longer sides and two oppositely arranged shorter sides. In this case, the first and second lateral regions may be positioned at or adjacent to the respective longer sides of said rectangular outline.

Similarly, the bone plate can have an outline with at least a first and second axis of symmetry, the extension along one of said axes of symmetry being larger than an extension along the respective other axis. For reasons of brevity, such a design will be referred to as the outline having a "short" and a "long" axis of symmetry in the following. This may apply, for example, to a bone plate having a substantially oval or elliptical outline. In these cases, the first and second lateral regions may be provided at or adjacent to regions of the outline that extend along (e.g., substantially parallel to) the longer axis of symmetry.

The region in which the first and second guiding channel axes cross each other may be provided in or at the front side or at least close to a respective surface portion thereof. Generally, the guiding channel axes may cross each other without actually intersecting, for example when extending at different height levels through the bone plate. The guiding channel axes may cross each other in a common channel portion of the first and second guiding channels. In this case, the first and second guiding channels comprise a common portion for receiving and guiding the flexible elongated member therethrough. In other words, the first and second guiding channels may merge into each other in at least one region for forming the common channel portion. In this case, the guiding channel axes can also intersect one another.

In this context, the common channel portion can be configured as a recess at the front side. The recess may take any shape and is for example configured with a substantially rectangular, oval or circular outline. Also, it can be substantially centrally located at the front side. According to one variant, the recess is configured as a through-hole. According to another variant, the recess is closed at one end (e.g., it may be pot-shaped). In general, the recess may connect the two guiding channels by forming a common free space in the form of the common channel portion through which both of the first and second guiding channel axes extend.

In addition, each guiding channel may comprise at least two elongated channel segments extending from different positions of the recess to the first and second lateral region of the bone plate, respectively. Therefore, the guiding channels may comprise at least one segment leading into and one segment leading out of the recess. The positions at which the two channel segments extend from the recess and/or merge therewith may be arranged substantially opposite to one another. For example, said positions may be located at opposite lateral regions of the recess.

The bone plate may comprise a cap member which is rotatably received in the recess. For doing so, the cap member can be received by means of a press- and/or form-fit which allows for a rotation in the recess. Specifically, the cap member may be rotatable about an axis extending transverse to the bone plate and/or at least one of the bone facing side and front side (e.g., extending substantially orthogonal thereto). The cap member may be configured to maintain its position within the recess after being rotated to a particular angular position (e.g., with help of a respective form- and/or press-fit).

The cap member may be formed of a plastics or polymer material. The bone plate may generally comprise metallic materials, such as titanium or titanium foam.

The cap member further may comprise at least one guiding opening which is selectively alignable with one of the guiding channels axes. The guiding opening can be configured as a channel, an aperture or a cut-out within the cap member. Also, the guiding opening may at least partially be formed in a sidewall portion of the cap member which is received in and/or abuts against the recess. In one example, the cap member comprises two guiding openings which are, for example, positioned substantially opposite to one another.

By rotating the cap member within the recess, the at least one guiding opening can be selectively aligned with one of the segments of the guiding channels extending from the recess. Hence, a flexible elongated member received in the respective guiding channel can extend through said guiding opening. At the same time, the cap member may be configured to block the passage through other guiding channel segments which are not aligned with the guiding opening.

The cap member may be removably mounted in the recess. In this manner, the bone plate can selectively be configured with our without the cap member depending on current needs. For doing so, a snap-in connection or a screw connection may be provided.

Each guiding channel axis may have a substantially continuously curved course or a substantially straight course. Accordingly, the guiding channels can be configured to guide the elongated member between the lateral regions of the bone plate in a substantially continuously curved or a substantially straight manner In one design, at least one of the guiding channels comprises a groove in the front side of the bone plate. The groove can be configured with a tapered cross-section. In one example, each guiding channel comprises two grooves extending from different and, preferably, opposite positions of a recess at the front side as discussed above.

Two neighbouring guiding channel axes may enclose an angle with one another of between approximately 10° and approximately 170°. In case only two guiding channels are provided, said guiding channels may enclose an angle of between approximately 30° and 120° or, preferably, of between approximately 45° and 90°. Said angle can generally be measured between respective guiding channel segments extending from the same lateral region of the bone plate and towards the region of crossing each other.

The bone plate may also comprise a third elongated guiding channel extending between the first to the second lateral region of the bone plate and comprising at least one segment extending in a region between the first and second guiding channel. The third guiding channel can have a third guiding channel axis that crosses the first and second guiding channel axes in the same region as they cross each other. Other than that, the third guiding channel can extend in a region of the bone plate (e.g., of the front side) being located between the first and second guiding channel In one example, the third guiding channel axis encloses a substantially similar angle with each of the first and second guiding channel axes, for example, an angle of between approximately 20° and 80°. Accordingly, the third guiding channel can generally extend in the middle between the first and second guiding channel.

The bone facing side may comprise a base portion and a plurality of spacer members protruding therefrom, the spacer members each being configured with a distal end portion facing the bone. The spacer members can be configured as substantially cylindrical and/or pillar-shaped members protruding transversely from the base portion towards an adjacent bone at which the bone plate is to be arranged. In one variant, the spacer members protrude substantially orthogonally from the base portion. The spacer members can be integrally formed with any of the base portion and/or the bone facing side and/or the bone plate.

The distal end portion can be arranged substantially opposite to that portion of the spacer members which is connected to and/or merges into the base portion (i.e., said end portion being "distal" with respect to the base portion). In one variant, the distal end portion is configured as a free end portion of the spacer members (e.g., to directly contact the bone). Alternatively, the distal end portion can be connected to further members which are actually provided for directly contacting the bone, such as an additional plate member. Said connection can be achieved by forming the distal end portions integrally with the additional bone contacting members.

According to one design, the distal end portions each comprise a spike. The spikes can hence form the actual free distal end portions of the spacer members. Again, the spikes can be integrally formed with said distal end portions and/or spacer members. Furthermore, the spikes may be configured to at least partially penetrate an adjacent bone surface to secure the position of the bone plate thereat.

A step may be provided between each distal end portion and an adjacent portion of the associated spacer member. Specifically, the adjacent portion may be configured with larger cross-sectional dimensions compared to the distal end portions (or vice versa), said difference in terms of cross-sectional dimensions resulting in the formation of the step.

For example, the adjacent portion may be configured with a larger diameter than the distal end portion. The step may form a stop face for contacting an adjacent bone surface. In this manner, the step may be configured to limit the penetration depth of the distal end portions into said bone surface, for example, in case the distal end portions comprise or are configured as a spike.

The bone facing side may comprise a porous material. The porous material may generally be arranged in a region of the bone facing side which is configured to contact the bone or at least be arranged adjacent thereto. The porous material may comprise a foamed material and/or an as such solid material being provided with dedicated cut-outs, apertures or the like for creating the porosity. The porosity can be provided in a substantially regular or irregular manner within the material, for example, with a substantially regular or irregular distribution and/or density of pores. Also, the porosity of said material may be selected so as to promote an in-growth of bone tissue.

Any of the base portion, the spacer members and/or their distal end portions may comprise a respective porous material. Specifically, in case the distal end portions comprise spikes, said spikes may comprise or be made of the porous material.

Also provided in a bone plate system comprising a first bone plate as described above and configured to be arranged at a region of bone, and further comprising a second plate configured to be arranged at an opposite circumferential region of the bone. The bone plate system may further comprise a flexible elongated member configured to be wound around the first and second bone plate so as to keep both bone plates in a fixed relative position to each other and to the bone.

According to a further aspect, a bone plate is provided, comprising a bone facing side comprising a base portion and one or more spacer members protruding therefrom, a front side being arranged substantially opposite to and facing away from the bone facing side, and a porous plate member connected by the one or more spacer members to the bone facing side. The bone facing side, the front side, the spacer members as well as the bone plate as such (e.g., its shape or material) can be configured as discussed above. Furthermore, the connection between the spacer members and the porous plate member can be achieved by forming said members integrally with one another. Moreover, the bone facing side and/or the porous plate member may be configured with (e.g., stepped) spikes for contacting the bone.

The porous plate member can be configured to extend substantially in parallel to the bone facing side and/or the front side. In one example, the porous plate member is substantially congruent with the bone facing side and/or the front side. In general, the size or, more specifically, the area covered by said porous plate member may at least be approximately 30% and, preferably, between approximately 60% to 100% of the area covered by the bone facing side and/or the front side. Note that the term "covered area" may generally refer to the bone area that can be covered when placing the bone plate at a bone or, in other words, be defined as the footprint of the respective portions of the bone plate. As a general matter, the porous plate member can be configured by a plurality of single plate members and/or single plate member sections which, taken together, define an area of any of the above discussed sizes.

Each spacer member may be configured to be severed by a separation tool. For example, each spacer member may have along its axial extension a weakened portion (e.g., of a reduced diameter).

According to a further aspect, a surgical kit assembly is provided, comprising a bone plate with a porous plate member as presented herein, and a separation tool configured to be insertable into the space between the porous plate member and the base portion of the bone facing side, the separation tool being configured to separate the porous plate member from the base portion.

The separation tool can be specifically sized and/or shaped to be insertable into the space between the porous plate member and the respective base portion. Said space can at least partially be defined by an axial length of the spacer members. Specifically, the thickness or material strength of the separation tool may be adapted to said space as well as a possible bend or curved shape thereof. Of course, the separation tool may be integrally formed with or connected to further members and/or portions which are not insertable into the relevant space, such as additional handling or gripping portions.

The separation tool can be configured as plate-type member and/or chisel-type tool and be manually insertable into the relevant space. Following that, a force can be exerted by manually pushing the separation tool against the spacer members. Alternatively, a hammer or the like can be used. In this way, the spacer members can be severed (e.g., cut and/or broken), thereby separating the porous plate member from the base portion.

The separation tool may further comprise a cutting edge for severing the spacer members. The cutting edge may be provided at a lateral region of the separation tool (e.g., formed by a tapered side face thereof). The cutting edge may be positioned at the separation tool so as to contact the spacer members substantially in or adjacent to a region in which they are connected to the porous plate member, e.g. at their distal end portions.

BRIEF DESCRIPTION OF THE DRAWINGS

Further details, advantages and aspects of the present disclosure will become apparent from the following embodiments taken in conjunction with the drawings, wherein.

DETAILED DESCRIPTION

In the following, embodiments of a bone plate and of a bone plate system as well as a surgical assembly kit comprising said bone plate will be described. The same reference numerals will be used to denote the same or similar structural features.

Figure 1:
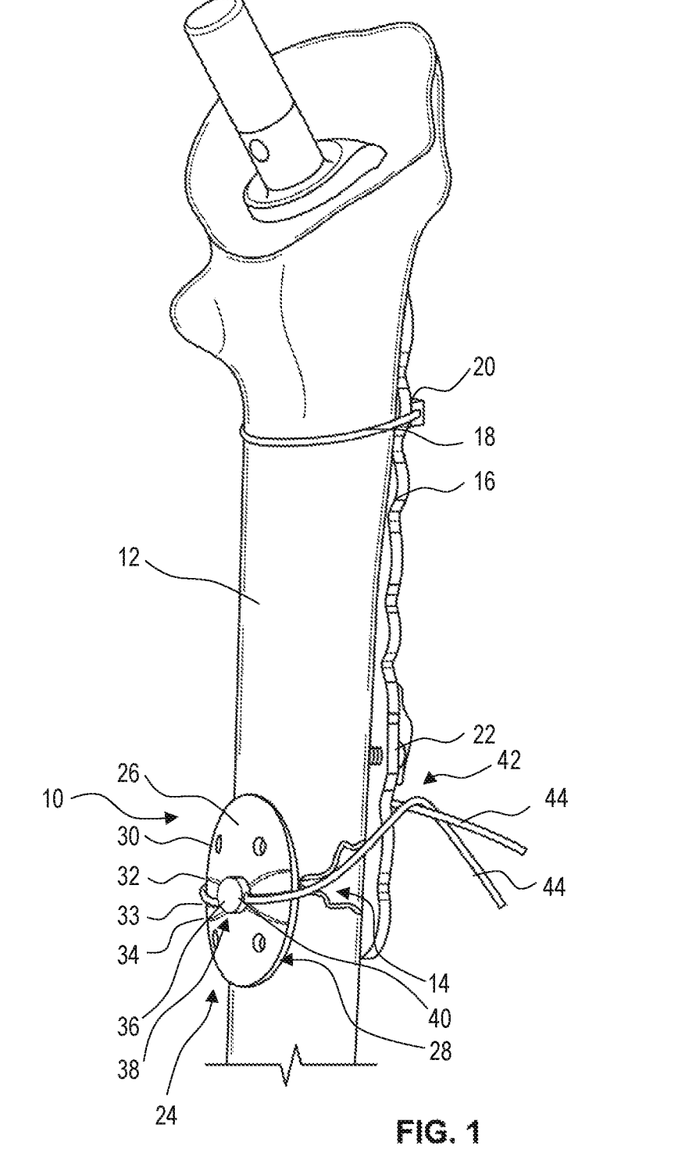
FIG. 1 shows a schematic illustration of a first embodiment of the bone plate being arranged at a fragmented bone.

FIG. 1 shows a perspective view of a bone plate 10 according to an embodiment with the bone plate 10 being positioned at a fragmented thigh bone 12. As can be gathered from FIG. 1, the bone plate 10 is directly positioned at a fragmented region 14 and contacts an outer circumferential surface of the bone 12.

Furthermore, a partially visible second bone plate in form of a primary plate 16 is provided. The primary plate 16 extends along a significantly longer portion of the bone 12 as compared to the bone plate 10. The bone plate 10 and the primary plate 16 define an embodiment of a bone plate system. They are arranged at opposite circumferential regions of the bone 12, thus facing in different and oppositely oriented directions. In this way, the bone plate 10 and the primary plate 16 are arranged so that they clamp the fragmented region 14 of the bone 12 between each other.

The primary plate 16 is held at the bone 12 by means of an upper circumferential wire 18. The circumferential wire 18 is connected to the primary plate 16 in a known manner, for example by means of a crimping member 20. Also, the circumferential wire 18 is tightened to hold the primary plate 16 in close contact with the adjacent bone surface. Furthermore, the primary plate 16 is connected to the bone 12 by means of one or more bone screws 22 inserted via a through-hole of the primary plate 16 into the bone 12.

The bone plate 10 is configured with an oval main body 24 having a front side 26 facing away from the bone 12 and towards the viewer. The main body 24 further comprises a bone facing side 28 which faces towards and contacts the bone 12 (not visible in FIG. 1). Furthermore, four through-holes 30 are provided in the bone plate 10 which are configured to receive a bone screw similar to the screw 22 penetrating the primary plate 16.

As will be described below, the bone plate 10 further comprises a first, second and third guiding channel 32, 34, 33. Moreover, a cap member 36 is provided which is inserted into a central recess being formed by a through-hole 38 in the front side 26 of the bone plate 10 (said through-hole 38 not being visible in FIG. 1). The cap member 36 further comprises two guiding openings 40 being arranged oppositely to one another, only one of which can be seen in FIG. 1.

In the depicted state, the guiding openings 40 are aligned with the third guiding channel 33 so that a further circumferential wire 42 can be inserted into to the guiding channel 33 and guided through the cap member 36. As indicated in FIG. 1, the circumferential wire 42 can thus be wound around a cross-section of the bone 12 as well as an opposite portion of the primary plate 16. Following that, the circumferential wire 42 can be tightened by connecting its free end portions 44 in a known manner (e.g., using an additional crimping member 20 or by making a knot).

Figure 2:
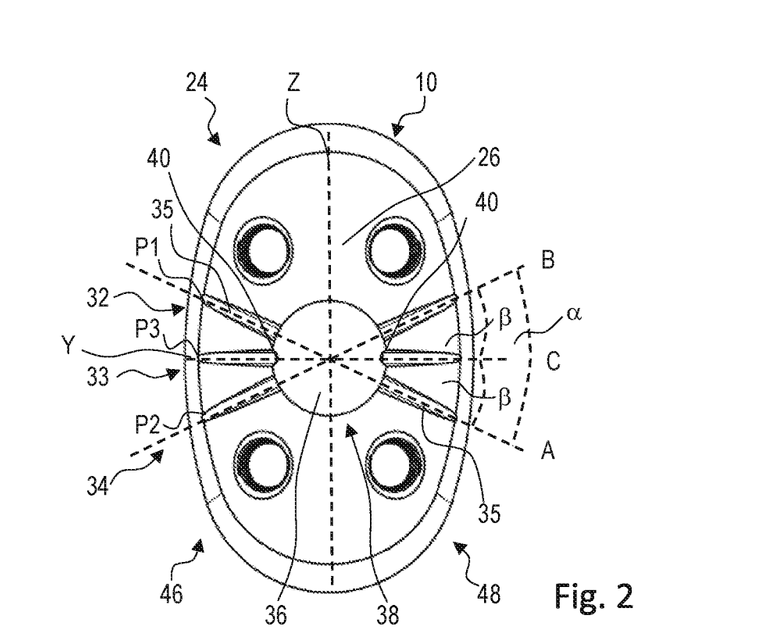
FIG. 2 shows a view of the front side of the bone plate according to FIG. 1.

FIG. 2 shows a view of the front side 26 of the bone plate 10 according to FIG. 1 from above. Again, the oval outline of the main body 24 can be seen having a longer axis of symmetry Z and a shorter axis of symmetry Y. Two lateral regions 46, 48 being opposite to one another extend substantially parallel to said longer axis of symmetry Z. The guiding channels 32, 33, 34 each extend between the lateral regions 46, 48 and each define a guiding channel axis A, B, C extending across the front side 26 from above. More specifically, the first guiding channel 32 defines the guiding channel axis A, the second guiding channel 34 defines the guiding channel axis B and the third guiding channel 33 defines guiding channel axis C. The guiding channel axes A, B, C cross each other in the region of the central through-hole 38 (obstructed by the cap member 36 in FIG. 2).

In more detail, each of the guiding channels 32, 33, 34 comprises two channel portions being configured as grooves 35 in the front side 26. The grooves 35 each extend from opposite positions of the through-hole 38 to one of the lateral regions 46, 48. Note that in FIG. 2, only the grooves 35 of the first guiding channel 32 are indicated by respective reference signs.

The grooves 35 merge into the through-hole 38, so that—at least without the optional cap member 36 detailed below—the wire 42 of FIG. 1 can generally be guided along any of the guiding channel axes A, B, C from one lateral region 46, 48 to the other while extending across the through-hole 38. The through-hole 38 thus defines a common channel portion of the guiding channels 32, 33, 34. In other words, the guiding channels 32, 33, 34 are each formed as a free space in the front side 26, said space being defined in each case by the above-described arrangement of two grooves 35 merging into the central through-hole 38. As detailed below, the guiding channels 32, 33, 34 can also partially be formed in or be obstructed by the cap member 36 depending on its rotational position within the central through-hole 38.

As further indicated in FIG. 2, the first and second guiding channels 32, 34 extend from positions P1 and P2 of the lateral regions 46, 48 which are spaced apart from the shorter axis of symmetry Y. Also, with respect to the respective axes of symmetry Y, Z, the first and second guiding channels 32, 34 generally extend diagonally across the front side 26.

The third guiding channel 33, on the other hand, extends from a position P3 being located on the shorter axis of symmetry Y. Also, its guiding channel axis C is parallel with said axis of symmetry Y and in the given case even coincides therewith. The third guiding channel axis C thus extends across the front side 26 and the central through-hole 38 from one lateral region 46, 48 to the other with the shortest possible length. Also, the groove segments 35 of the third guiding channel 33 extend in a region of the front side 26 being located between the first and second guiding channels 32, 34.

Moreover, FIG. 2 shows that the first and second guiding channel axes A, B enclose an angle α with one another of 60°. This angle α is measured between respective groove segments 35 of these channels 32, 34 being arranged at the same side of the through-hole 38 or, with reference to FIG. 2, extending from the same lateral region 48. Similarly, the third guiding channel axis C encloses an angle β with each of the first and second guiding channel axis A, B of 30°. The groove segments 35 of the third guiding channel 33 are thus arranged in the middle between the respective groove segments 35 of the first and second guiding channels 32, 34.

Overall, the arrangement of the crossing guiding channels 32, 33, 34 according to this embodiment thus allows for a compact design of the bone plate 10, while offering various possibilities for fixing the bone plate 10 with a circumferential wire 42.

In FIG. 2, the cap member 36 is positioned within the through-hole 38 so that its guiding openings 40 are aligned with each of the groove segments 35 of the third guiding channel 33. As described below, a free space in form of a non-illustrated slot 60 is provided in the cap member 36 and connects the two guiding openings 40 with one another.

Starting from the left lateral region 46 in FIG. 2, the wire 42 of FIG. 1 can hence be guided along the third guiding channel axis C by inserting it into the left groove segment 35 of the third guiding channel 33, through the guiding openings 40 and slot 60 of the cap member 36 and thus across the central through-hole 38 and finally into the right groove segment 35 for guiding it towards the second lateral region 48.

At the same time, since the guiding openings 40 are not aligned with any of the groove segments 35 of the first or second guiding channel 32, 34, it is not possible to guide the wire 42 along the respective first and second channel axes A, B. Rather, the cap member 36 obstructs said remaining guiding channels 32, 34 or, in other words, intersects the respective channel axes A, B by means of a solid sidewall section 71 (not depicted in FIG. 2).

Other possibilities for applying a circumferential wire 42 include guiding the wire 42 twice around the bone 12 and bone plate 10 to form a cross. In this case, the cap member 36 of FIG. 2 may be omitted. Instead, the wire 42 is inserted into the left groove segment 35 of the first guiding channel 32 at position P1, guided along the first channel axis A while crossing the central through hole 38, to then exit the first guiding channel 32 at the opposite lateral region 48. Following that, the wire is circumferentially wrapped around the bone 12 and brought back to the bone plate 10 at position P2 for entering the second guiding channel 34. Again, the wire 42 is then guiding along the respective guiding channel axis B towards the opposite lateral region 48. Note that in this process, it crosses the wire section that is accomated in the first guiding channel 32 in the region of the central through-hole 38. Said through hole 38 hence defines a free space for accommodating the crossing wire sections, thus limiting a formation of bulges or protrusions by said wire sections at the front side 26. After forming the cross, the free-ends of the wire 42 are secured to each other in the region of the primary plate 16 in FIG. 1, for example, by crimping.

Of course, it is also possible to form a similar cross by guiding the wire 42 through two different guiding channels 32, 33, 34 or even through all of the guiding channels 32, 33, 34 by wrapping it a third time around the bone 12.

A further alternative includes using two or even three separate circumferential wires 42, each being guided through one of the guiding channels 32, 33, 34. In other words, further to the circumferential wire 42 of FIG. 1 which is accommodated in the third guiding channel 33, a second wire 42 can be guided through the first guiding channel 32 and crimped or knotted at a similar position at the primary plate 16. The cap member 36 of FIG. 2 may again be omitted in this case. Also, a third wire 42 may be guided through the second guiding channel 34 and be secured in a similar manner Again, the crossing portions of the wires 42 are accommodated in the central through-hole 38, thus limiting bulges or protrusions. Also, any of the guiding channels 32, 33, 34 may be selected and combined for accommodating one of a respective plurality of separate circumferential wires 42.

Figure 3:
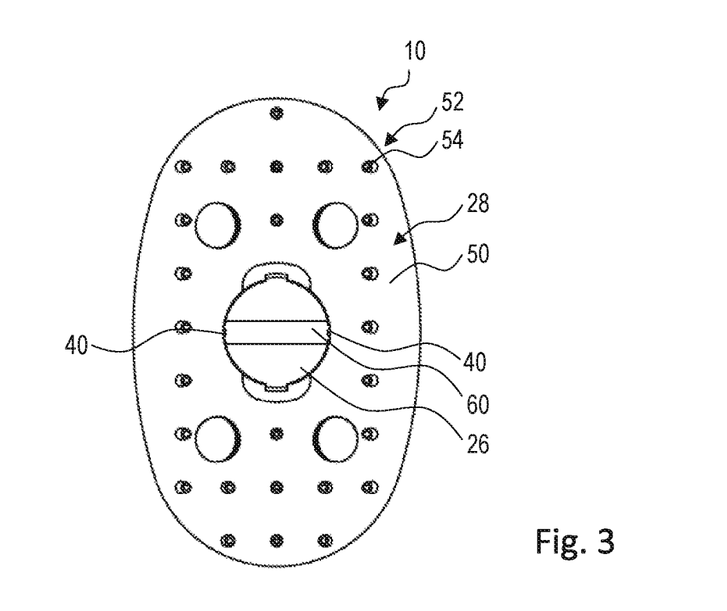
FIG. 3 shows a view of the bone facing side of the bone plate according to FIG. 1.

FIG. 3 shows a rear view of the bone plate 10 according to FIGS. 1 and 2 onto the bone facing side 28. The bone facing side 28 comprises a base portion 50 with a plurality of spacer members 52 protruding therefrom towards an adjacent bone surface at which the bone plate 10 is to be arranged. In the depicted embodiment, the spacer members 52 are provided with spikes 54 at distal end portions thereof (see also following discussion). Furthermore, the portion of the cap member 36 facing the bone 12 of FIG. 1 can be seen. As previously discussed, said portion is configured with an elongated straight slot 60 which connects the guiding openings 40 with one another.

Figure 4:
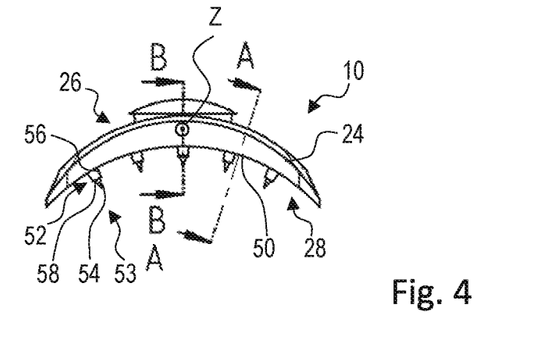
FIG. 4 shows a side view of the bone plate according to FIG. 1 indicating the position of the sectional views B-B and A-A according to FIGS. 5 and 6.

FIG. 4 shows a side view of the bone plate 10 with the longer axis of symmetry Z of FIG. 2 extending directly towards the viewer. It can be seen that the main body 24 of the bone plate 10 is convexly curved with the bone facing side 28 being arranged at a radially inner portion and the front side 26 being arranged in a radially outer portion thereof. Furthermore, it can be seen that the spacer members 52 are configured with spikes 54 at their distal end portions 53. More specifically, the spacer members 52 comprise a cylindrical base 56 protruding from the base portion 50 of the bone facing side 28 and towards the non-illustrated bone 12 (cf. FIG. 1). The diameter of said base 56 generally exceeds the largest diameter of the spikes 54, such that a step 58 is formed between these portions. The step 58 acts as a stop face when arranging the bone plate 10 at the bone 12 and pushing the spikes 54 into the adjacent bone surface.

Figure 5:
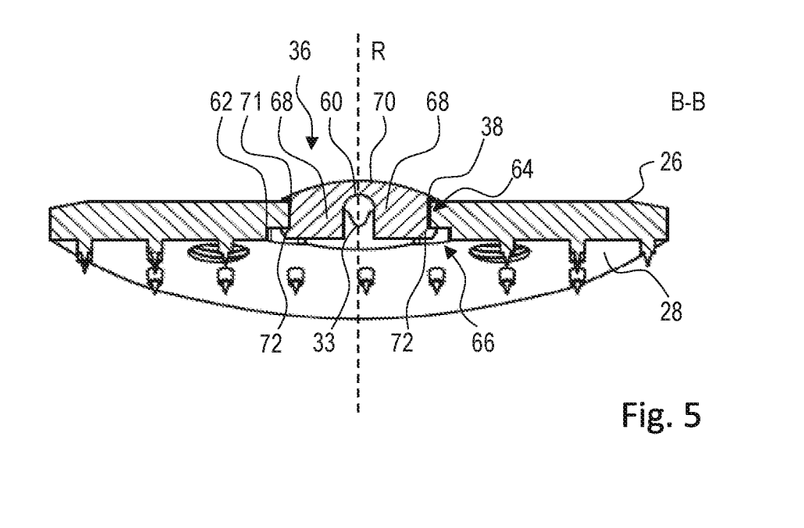
FIG. 5 shows a view according to section B-B of FIG. 4.

In FIG. 4, a section B-B is indicated which is depicted as a corresponding sectional view B-B in FIG. 5. In this view, the central trough-hole 38 for receiving the cap member 36 can clearly be seen. The trough-hole 38 is provided with a diameter step 62 close to the bone facing side 28. This step 62 results from providing a first section 64 of the trough-hole 38 in the region of the front side 26 with a smaller diameter compared to a second section 66 in the region of the bone facing side 28. The resulting diameter step 62 thus provides an undercut for snapping the cap member 36 into the through-hole 38.

For doing so, the cap member 36 is provided with two flexible leg portions 68 which are separated by the above-discussed slot 60. The leg portions 68 are connected by a dome-shaped top portion 70 of the cap member 36, said portion 70 being arranged at the front side 26 of the bone plate 10. At their free end portions remote from the dome-shaped top portion 70, the leg portions 68 are configured with protruding sections 72. By elastically deforming the cap member 36, for example, by pushing the leg portions 68 slightly towards each other, the protruding sections 72 can be inserted into the trough-hole 38 and engage with the undercut 62. The cap member 36 is thus releasably held in the trough-hole 38. Furthermore, a sidewall section 71 of each leg portion 68 is pushed against the first section 64 of the trough-hole 38, thus producing a frictional contact.

As a result, the cap member 36 can be rotated about a rotational axis R extending orthogonally to an adjacent region of the front side 26 and bone facing side 28. A rotational position of the cap member 36 within the trough-hole 38 can be maintained by means of the above-discussed frictional contact. This way, the slot 60 and the receiving openings 40 can be selectively aligned with one of the guiding channel axes A, B, C as explained above. Similar to the previous drawings, in the depicted state the slot 60 is aligned with the third guiding channel axis C, so that a wire can be guided through the third guiding channel 33.

Figure 6:
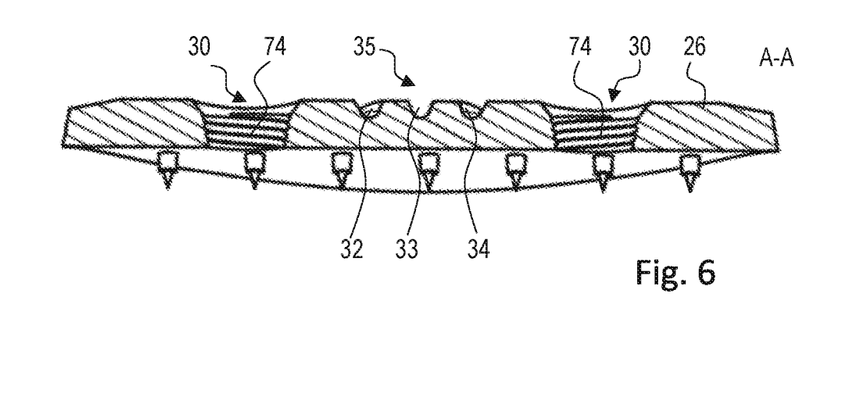
FIG. 6 shows a view according to section A-A of FIG. 4.

FIG. 6 shows the sectional view A-A as indicated in FIG. 4. It is shown that the through-holes 30 for receiving bone fixation screws 22 are configured with a thread 74 for cooperating with a complementary thread (not shown) that is provided at the head of a bone screw to be inserted into the bone 12 via a particular one of the through-holes 30. Furthermore, it can be seen the groove segments 35 of the guiding channels 32, 33, 34 are configured with a tapered cross section or, in other words, with an increasing width towards an outer face of front side 26. This helps to securely hold the wire 42 in place.

Figures 7, 8:
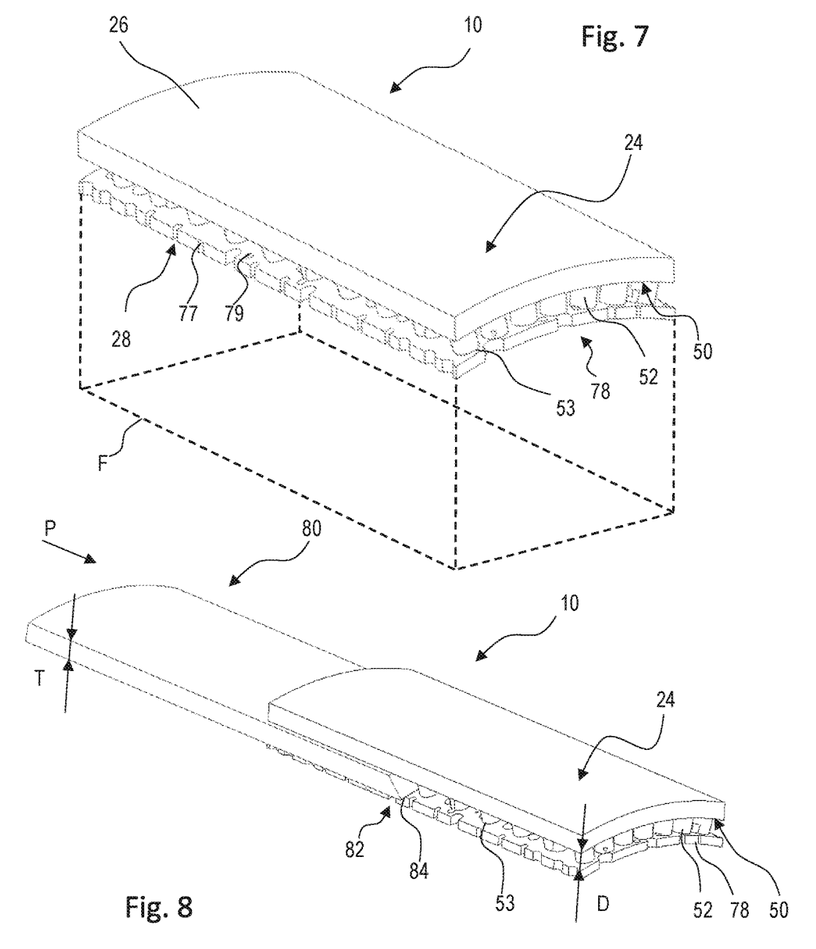
FIG. 7 shows a perspective view of a bone plate according to a second embodiment.
FIG. 8 shows a view of a surgical kit assembly comprising the bone plate according to FIG. 6 as well as a separation tool.

FIG. 7 depicts a bone plate 10 according to a further embodiment. The bone plate 10 again comprises a plate-type main body 24 with a front side 26 which, although not specifically illustrated, is configured with a similar guiding channel arrangement as previously discussed. Also, the bone plate 10 can be arranged at a bone 12 in a similar manner as discussed with reference to FIG. 1 and may form a bone plate system with a further bone plate (reference numeral 16 in FIG. 1).

The bone plate 10 further comprises a bone facing side 28 with a base portion 50, the latter also forming part of the main body 24. Also, several cylindrical spacer members 52 protrude from said base portion 50. Yet, instead of being configured with spikes 54, the distal end portions 53 of the spacer members 52 are connected to a common porous plate member 78. Said porous plate member 78 is shaped and sized similarly to the main body 24 and the front portion 26. Specifically, it is provided with a similar convex curvature and covers a similar area F. Also, the porous plate member 78 generally extends in parallel with the front side 26 and main body 24. Note that the porosity of the porous plate member 78 is provided by means of several dedicated cut-outs 77 and apertures 79.

According to this embodiment, the bone plate 10 is to be arranged at a bone 12 so that the porous plate member 78 directly contacts the adjacent bone surface. The porosity of the plate member 78 is selected to promote an in-growth of bone tissue. This further promotes the stabilization and thus the healing process of a respectively fragmented bone section 14. Yet, to avoid damages when removing the bone plate 10 from the bone 12, the bone plate 10 of this embodiment is generally configured to be separable into at least two parts.

This is accordingly depicted in FIG. 7 showing a surgical assembly kit, comprising the bone plate 10 of FIG. 6 and a separation tool 80. The separation tool 80 is configured as a plate-type member having a convex curvature that corresponds to the shape of the main body 24 and porous plate member 78 of the bone plate 10. Furthermore, the thickness T of the separation tool 80 is smaller than a distance D between the plate member 78 and the main body 24 as defined by the spacer members 52. In other words, with help of the spacer members 52, the main body 24 or, more specifically, the base portion 50 of the bone facing side 28, and the porous plate member 78 are positioned at a distance D to one another, thus defining a space between them into which the separation tool 80 can be inserted.

As further illustrated in FIG. 7, the separation tool 80 is provided with a tapered front face 82 defining a cutting edge 84. In the depicted state, the cutting edge 84 is arranged close to a region in which the spacer members 52 merge into the porous plate member 78, i.e., close to the distal end portions 53 of the spacer members 52. Therefore, when exerting a pushing force P onto the separation tool 80, the cutting edge 84 is pushed against the spacer members 52, thus being able to cut through and sever them. This way, the porous plate member 78 can be separated from the base portion 50 and the main body 24. In consequence, the main body 24 as well as large parts of the spacer members 52 can be removed from the bone 12, whereas the partially ingrown porous plate member 78 can remain thereat.

In the forgoing, embodiments and variants of embodiments have exemplarily been described. The present invention should not be construed as being limited to the particular embodiments and their variants as discussed herein. Rather, it will be appreciated that various changes and modifications may be made by a person skilled in the art without departing from the scope of the present invention as defined in the claims that follow.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone plate, comprising:
a bone facing side,
a front side arranged substantially opposite to and facing away from the bone facing side, and
at least a first and a second elongated guiding channel, the first and second elongated guiding channels each being configured to receive a flexible elongated member,
the first and second elongated guiding channels each further being configured to guide said elongated member along a respective first and second guiding channel axis from a first to a second lateral region of the bone plate,
the first and second elongated guiding channel axes crossing each other in at least one region of the bone plate, the at least one region being configured as a recess at the front side,
and the bone plate further comprising a cap member which is rotatably received in the recess and includes at least one guiding opening.

2. The bone plate according to claim 1, wherein the elongated guiding channel axes cross each other in a common channel portion of the first and second elongated guiding channels.

3. The bone plate according to claim 1, wherein each elongated guiding channel comprises at least two elongated channel segments extending from different positions of the recess to the first and second lateral regions of the bone plate, respectively.

4. The bone plate according to claim 1, wherein the at least one guiding opening is configured to be selectively alignable with one of the elongated guiding channel axes.

5. The bone plate according to claim 1, wherein the cap member is removably mounted in the recess.

6. The bone plate according to claim 1, wherein each elongated guiding channel axis has a substantially continuously curved course or a substantially straight course.

7. The bone plate according to claim 1, wherein at least one of the elongated guiding channels comprises a groove in the front side of the bone plate.

8. The bone plate according to claim 1, wherein two neighboring elongated guiding channel axes enclose an angle with one another of between approximately 10° and approximately 170°.

9. The bone plate according to claim 1, wherein the bone plate comprises a third elongated guiding channel extending between the first and the second lateral regions of the bone plate and comprising at least one segment extending in a region between the first and second elongated guiding channel.

10. The bone plate according to claim 1, wherein the bone facing side comprises a base portion and plurality of protrusions, the protrusions each being configured with a distal end portion configured for facing the bone.

11. The bone plate according to claim 10, wherein the distal end portions each comprise a spike.

12. The bone plate according to claim 10, wherein a step is provided between each distal end portion and an adjacent portion of respective protrusion.

13. The bone plate according to claim 1, wherein the bone facing side comprises a porous material.

14. A bone plate system, comprising:
a first bone plate according to claim 1 and configured to be arranged at a region of bone; and
a second bone plate configured to be arranged at an opposite circumferential region of the bone.

15. A bone plate, comprising:
a bone facing side comprising a base portion and one or more protrusions,
a front side being arranged substantially opposite to and facing away from the bone facing side, and
a porous plate member connected by the one or more protrusions to the bone facing side.

16. The bone plate according to claim 15, wherein each protrusion is configured to be severed by a separation tool.

17. A surgical kit assembly, comprising:
a bone plate according to claim 15;
a separation tool configured to be insertable into the space between the porous plate member and the base portion of the bone facing side,
the separation tool being configured to separate the porous plate member from the base portion.

18. The surgical kit assembly according to claim 17, wherein the separation tool comprises a cutting edge for severing the protrusions.

19. A surgical kit comprising:
a bone plate comprising:
a bone facing side including a base portion,
a front side arranged substantially opposite to and facing away from the bone facing side, and
at least a first and a second elongated guiding channels, the first and second elongated guiding channels each being configured to receive a flexible elongated member,
the first and second elongated guiding channels each further being configured to guide said elongated member along a respective first and second guiding channel axis from a first to a second lateral region of the bone plate,
the first and second elongated guiding channel axes crossing each other in at least one region of the bone plate;
a porous plate and a spacer member intermediate the bone facing side of the bone plate and the porous plate;
a separation tool configured to be insertable into the space between the porous plate member and the base portion of the bone facing side; and
the separation tool being configured to separate the porous plate member from the base portion.

20. A bone plate, comprising:
a bone facing side,
a front side being arranged substantially opposite to and facing away from the bone facing side, and
at least a first, a second and a third elongated guiding channel, the first, second and third guiding channels each being configured to receive a flexible elongated member,
the first, second and third elongated guiding channels each further being configured to guide said elongated member along a respective first, second and third elongated guiding channel axis from a first to a second lateral region of the bone plate,
the first, second and third elongated guiding channel axes crossing each other in at least one region of the bone plate.

21. The bone plate of claim 20, wherein the third elongated guiding channel comprises at least one segment extending in a region between the first and second elongated guiding channels.

22. A bone plate, comprising:
a bone facing side,
a front side being arranged substantially opposite to and facing away from the bone facing side, and
at least a first and second elongated guiding channel, the first and second elongated guiding channels each being configured to receive a flexible elongated member,
the first and second elongated guiding channels each further being configured to guide said elongated member along a respective first and second elongated guiding channel axis from a first to a second lateral region of the bone plate,
the first and second elongated guiding channel axes crossing each other in at least one region of the bone plate,
the first and second elongated guiding channel axes crossing each other in a common channel portion of the first and second guiding channels, the common channel portion being configured as a recess at the front side, and
the bone plate further comprising a cap member which is rotatably received in the recess, the cap member comprising at least one guiding opening which is selectively alignable with one of the guiding channel axes.

23. A bone plate, comprising:
a bone facing side,
a front side being arranged substantially opposite to and facing away from the bone facing side, and
at least a first and a second elongated guiding channel, the first and second elongated guiding channels each being configured to receive a flexible elongated member,
the first and second elongated guiding channels each further being configured to guide said elongated member along a respective first and second guiding channel axis from a first to a second lateral region of the bone plate,
the first and second elongated guiding channel axes crossing each other in at least one region of the bone plate,
the first and second elongated guiding channel axes crossing each other in a common channel portion of the first and second guiding channels, the common channel portion being configured as a recess at the front side through which the first and second elongated guiding channel axes extend.

* * * * *